(12) United States Patent
Park et al.

(10) Patent No.: US 6,316,618 B1
(45) Date of Patent: Nov. 13, 2001

(54) PROCESS FOR PREPARING (-) PYRIDOBENZOXAZINE CARBOXYLIC ACID DERIVATIVES

(75) Inventors: Young-Jun Park; Ho-Seong Lee; Min-Hwan Kim, all of Taejon; Kyung-Chul Kim, Ulsan, all of (KR)

(73) Assignee: Samsung Electronics Co., Ltd. (KR)

( * ) Notice: Subject to any disclaimer, the term of this patent is extended or adjusted under 35 U.S.C. 154(b) by 0 days.

(21) Appl. No.: 09/674,323

(22) PCT Filed: Feb. 23, 2000

(86) PCT No.: PCT/KR00/00145

§ 371 Date: Oct. 24, 2000

§ 102(e) Date: Oct. 24, 2000

(87) PCT Pub. No.: WO00/50428

PCT Pub. Date: Aug. 31, 2000

(30) Foreign Application Priority Data

Feb. 24, 1998 (KR) .............................. 99-0006093

(51) Int. Cl.[7] ....................... C07D 498/06; C07D 403/10

(52) U.S. Cl. ........................................... 544/101; 544/363

(58) Field of Search ..................................... 544/363, 101

(56) References Cited

U.S. PATENT DOCUMENTS

| 4,382,892 | 5/1983 | Hayakawa et al. . |
| 4,762,831 | 8/1988 | Grohe . |
| 4,777,253 | 10/1988 | Mitscher et al. . |
| 4,859,773 | 8/1989 | Grohe et al. . |
| 4,958,045 | 9/1990 | Grohe et al. . |
| 5,237,060 | 8/1993 | Schriewer et al. . |
| 5,539,110 | 7/1996 | Kim et al. . |

FOREIGN PATENT DOCUMENTS

| 0 206 283 | 12/1986 | (EP) . |
| 2 301 354 | 12/1996 | (GB) . |
| 1-165589 A | 6/1989 | (JP) . |
| WO 90/12799 A1 | 11/1990 | (WO) . |

*Primary Examiner*—Emily Bernhardt
(74) *Attorney, Agent, or Firm*—Knobbe, Martens, Olson & Bear, LLP.

(57) ABSTRACT

Disclosed is a process for preparing optically active (−)pyridobenzoxazine carboxylic acid derivative and pharmaceutically acceptable salt thereof by employing a starting material of (+)ethyl 2-(4-chloro-5-fluoro-2-halo-3-nitobenzoyl)-3-[(1-hydroxypropy-2(s)-yl)amino]acrylate. According to the present invention, optically active (−)pyridobenzoxazine carboxylic acid derivative can be manufactured from low-priced 4-chloro-5-fluorobenzoic acid derivative in a simple and economical manner.

15 Claims, No Drawings

PROCESS FOR PREPARING (-) PYRIDOBENZOXAZINE CARBOXYLIC ACID DERIVATIVES

BACKGROUND OF THE INVENTION

1. Field of the Invention

The present invention relates to a process for preparing an optically active (−)9-fluoro-3-methyl-7-oxo-2,3-dihydro-7H-pyrido[2,3-de]([1,4]-benzoxazine-6-carboxylic acid derivative ("pyridobenzoxazine carboxylic acid derivative") represented by the formula (I) or pharmaceutically acceptable salt thereof having an excellent antimicrobial activity.

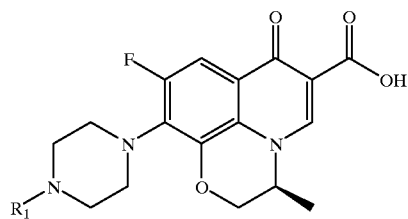

(I)

wherein, $R_1$ represents hydrogen atom or lower alkyl group having 1 to 5 carbon atoms.

2. Description of the Prior Art

A variety of optically active pyridobenzoxazine carboxylic acid derivatives have been prepared and used as active ingredients for antibiotic agents, since the compounds are known to possess higher antimicrobial activity and weaker toxicity than optically inactive racemic mixture(see: Drugs of the Future, 17 (2), 559–563 (1992)).

In general, optically active (−)pyridobenzoxazine carboxylic acid derivatives have been prepared in the art by the following two processes: the first one comprises a step of selective hydrolysis of (±)7,8-fluoro-2,3-dihydro-3-acetoxymethyl-4H-[(1,4]-benzoxazine by hydrolase; and, the second one comprises a step of optical resolution of (±)7,8-fluoro-2,3-dihydro-3-acetoxymethyl-4H-[1,4]-benzoxazine by chemical reagent (see: EP 206,283; Korean Pat. No. 60,571). However, those processes have several drawbacks as followings: 1) theoretically 50% of isomers are lost; 2) high-priced reagent for separation is used; and, 3) complicate process of 8 steps are accompanied, which is not suitable for industrial-scale mass production. To solve the said problems, a process has been developed to. prepare (−)isomer by racemizing (+)isomer obtained as a by-product during the said process (see: Japanese Patent Publication (Hei) 10-357910).

Further, processes for preparing optically active pyridobenzoxazine carboxylic acid derivatives are disclosed in U.S. Pat. Nos. 4,777,253 and 5,237,060 and Korean Pat. No. 125,115 as well. These prior arts suggest that optically active (−)pyridobenzoxazine carboxylic acid derivatives using optically active (L)-alaninol can be prepared without optical resolution, which is represented as the following reaction scheme:

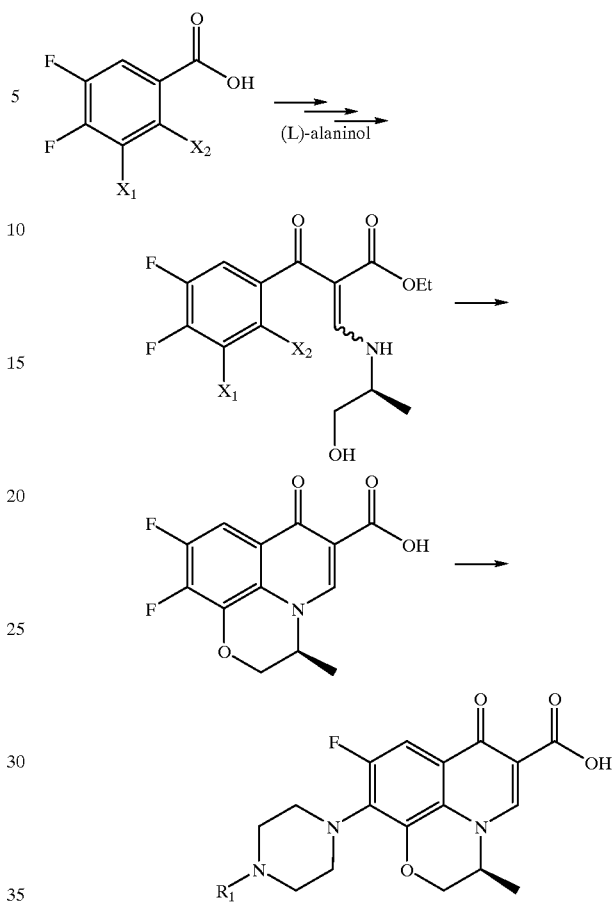

As shown in the scheme above, a starting material of 4,5-difluorobenzoic acid derivative should be employed in the reaction, since fluorine atom among various halogen atoms is essentially required for the last step of substituting proper piperazine for 10-halogen atom. Though this process is improved in a sense that optical resolution step is not necessary, it has revealed a critical demerit that very expensive 4,5-difluorobenzoic acid derivative is required. On the other hand, it has been reported that relatively inexpensive 4-chloro-5-fluorobenzoic acid derivative, whose reactivity is lowered than 4,5-difluorobenzoic acid derivative, leads to substitution reaction at 9-fluorine atom rather than 10-fluorine atom in the last step (see: Chem. Pharm. Bull., 32, 4907–4913 (1984)).

Therefore, there are strong reasons for exploring and developing a process for preparing optically active (−)pyridobenzoxazine carboxylic acid derivative by employing a low-priced material in a simple and economical manner.

SUMMARY OF THE INVENTION

The present inventors successfuly prepared optically active (−)pyridobenzoxazine carboxylic acid derivative, by employing a starting material of (+)ethyl 2-(4-chloro-5-fluoro-2-halo-3-nitobenzoyl)-3-[(1-hydroxypropy-2 (S)-yl) amino]acrylate which is obtainable from low-priced 4-chloro-5-fluorobenzoic acid derivative instead of high-priced 4,5-difluorobenzoic acid derivative, and substituting piperazine for chlorine atom.

A primary object of the present invention is, therefore, to provide a process for preparing optically active (−)pyridobenzoxazine carboxylic acid derivatives.

DETAILED DESCRIPTION OF THE INVENTION

The other object of the invention is to provide novel compounds which are available as intermediates in the course of preparing the (−)pyridobenzoxazine carboxylic acid derivatives.

In carrying out the present invention, a low-priced compound(V) is employed as a starting material which is obtainable from 4-chloro-5-fluoro-2-halo-3-nitrobenzoic acid derivatives by the known process in the art (see: U.S. Pat. No. 5,237,060). As shown in the reaction scheme below, optically active (−) pyridobenzoxazine carboxylic acid derivatives of the invention are prepared by the following steps: i) reacting a compound(V) with a reactive material (VI) or (VII) in the presence of a base to obtain a compound (IV); ii) converting the compound(IV) to a compound(III) in an organic polar solvent and in the presence of a base; iii) reacting the compound(III) with piperazine or N-mono-substituted-piperazine in an organic polar solvent in the presence of a base to obtain a novel compound(II) by so-called one-pot reaction; and, iv) hydrolyzing and cyclizing the compound(II) in an organic solvent in the presence of metal hydroxide to give the optically active compound(I).

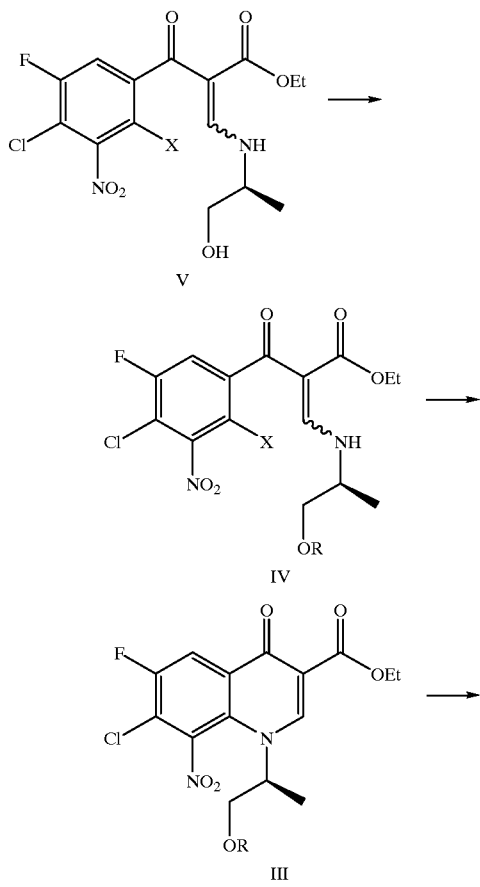

wherein,

X represents a halogen atom;

Z represents a leaving group;

Y represents an oxygen or a sulfur atom;

$R_a$ represents —C(=O)—$R_2$ [wherein $R_2$ represents an alkyl group having 1 to 5 carbon atoms, phenyl group, substituted phenyl group, alkoxy group having 1 to 5 carbon atoms, cycloalkoxy group having 3 to 5 carbon atoms, phenoxy group, substituted phenoxy group, primary or secondary amine group or alkylthio group having 1 to 5 carbon atoms];

$R_b$ represents alkyl group having 1 to 5 carbon atoms, phenyl group or substituted phenyl group;

R represents the same as Ra above or $R_b$—NH—C(=Y) [wherein $R_b$ and Y represent the same above]; and, $R_1$ represents hydrogen atom or alkyl group having 1 to 5 carbon atoms.

Specifically, X includes halogen atom such as chlorine atom and fluorine atom.

Z includes halogen atom such as chloride atom and fluorine atom; carboxylate group; and, alkoxy group.

$R_2$ includes lower alkyl group having 1 to 5 carbon atoms, such as methyl group, ethyl group, n-propyl group, isopropyl group, t-butyl group, sec-butyl group, n-butyl group, isobutyl group, t-pentyl group, n-pentyl group, isopentyl group and neopentyl group, preferably methyl group and ethyl group; phenyl group; substituted phenyl group such as p-methoxyl phenyl group, 3,5-dimethoxyphenyl group, 3,5-dimethylphenyl group, 2,4,6-trimethylphenyl group, p-chlorophenyl group and p-fluorophenyl group; alkoxy group having 1 to 5 carbon atoms such as methoxy group, ethoxy group, n-propoxy group, t-butoxy group, sec-butoxy group, n-butoxy group, isobutoxy group, t-pentoxy group, isopentoxy group, neopentoxy group and cyclopentoxy group; cycloalkoxy group having 3 to 5 carbon atoms such as cyclopropoxy group, cyclobutoxy group and cyclopentoxy group; phenoxy group; substituted phenoxy group such as p-methoxyphenoxy group, p-chlorophenoxy group and p-fluorophenoxy group; primary or secondary amine group such as methylamine group, dimethylamine group, ethylamine group and diethylamine group; and, alkylthio group having 1 to 5 carbon atoms such as methylthio group, ethylthio group, n-propylthiogroup, isopropylthio group, t-butylthio group, sec-butylthio group, n-butylthio group, isobutylthio group, t-pentylthio group, isopentylthio group and neopentylthio group.

$R_b$ inqludes lower alkyl group having 1 to 5 carbon atoms such as methyl group, ethyl group, n-propyl group, isopropyl group, t-butyl group, sec-butyl group, n-butyl group, isobutyl group, t-pentyl group, n-pentyl group, isopentyl group and neopentyl group; phenyl group; and, substituted phenyl group such as p-methoxyphenyl group, 3,5-dimethoxyphenyl group, 3,5-dimethylphenyl group, 2,4,6-trimethylphenyl group, p-chlorophenyl group and p-fluorophenyl group.

$R_1$ includes hydrogen atom and lower alkyl group having having 1 to 5 carbon atoms such as methyl group, ethyl group, n-propyl group, isopropyl group, t-butyl group, sec-butyl group, n-butyl group, isobutyl group, t-pentyl group, n-pentyl group, isopentyl group and neopentyl group.

The process for preparing optically active (−) pyridobenzoxazine carboxylic acid derivatives is described in more detail.

(1) Step 1: Preparation of Compound(IV)

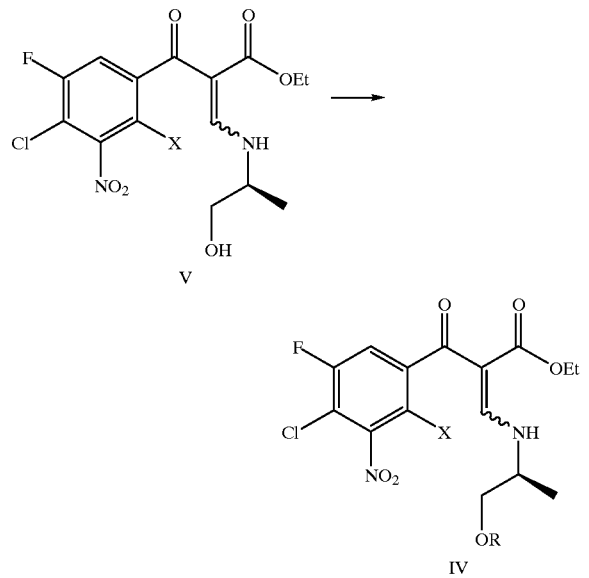

wherein,

X and R represent the same above.

Starting material(V) of (+)ethyl 2-(4-chloro-5-fluoro-2-halo-3-nitrobenzoyl)-3-[(1-hydroxypropy-2 (S)-yl) aminolacrylate which is obtained from 4-chloro-5-fluoro-2-halo-3-nitrobenzoic acid derivative by the conventional process (see: U.S. Pat. No. 5,237,060) is reacted with 1.0~3.0 mole equivalents of reactive material(VI) or (VII) in an organic solvent in the presence of a base at a temperature of −400° C. to 80° C. to obtain a compound(IV).

$R_a$—Z (VI)

$R_b$—N=C=Y (VII)

wherein $R_a$, $R_b$, Z, and Y represent the same above.

The reactive material(VI) includes acylhalide, carboxylic acid anhydride, alkylchloroformate, cycloalkylchloroformate, alkylcarbonate, cycloalkylcarbonate, phenylchloroformate, substituted phenylchloroformate; and, the reactive material(VII) includes isocyanate and isothiocyanate.

The base includes metal carbonate, metal bicarbonate, metal alkoxide, 1,8-diazabicyclo[5.4.0]-7-undecene (DBU), 1,4-diazabicyclo[2.2.2]octane (DABCO), 1,5-diazabicyclo [4.3.0]-5-nonene (DBN), pyridine, dimethylaminopyridine and trimethylamine, where potassium carbonate and sodium carbonate are preferably employed as the metal carbonate; potassium bicarbonate and sodium bicarbonate, as the metal bicarbonate; and, sodium methoxide and sodium ethoxide, as the metal alkoxide.

(2) Step 2: Preparation of Compound(III)

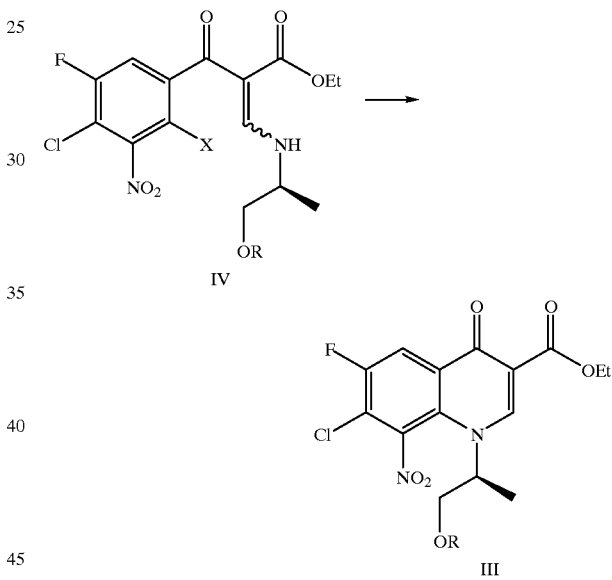

wherein,

X and R represent the same above,

The compound(IV) obtained in Step 1 is converted to a compound(III) in the presence of an organic polar solvent and 2.0~5.0 mole equivalents of base at a temperature of range of 18° C. to 150° C. depending on the solvent and the base.

The organic polar solvent includes DMF (N,N'-dimethylformamide), DMSG (dimethylsulfoxide), dioxane, acetonitrile, tetrahydrofuran and acetone. The base includes metal carbonate, metal bicarbonate, metal alkoxide, DBU (1,8-diazabicyclo[5.4.0]undec-7-ene), DABCO(1,4-diazabicyclo[2.2.2]octane, DBN(1,5-diazabicyclo[4.3.0] non-5-ene), pyridine, dimethylaminopyridine and trimethylamine, where the metal carbonate, the metal bicarbonate and the metal alkoxide are the same above.

(3) Step 3: Preparation of Compound(II)

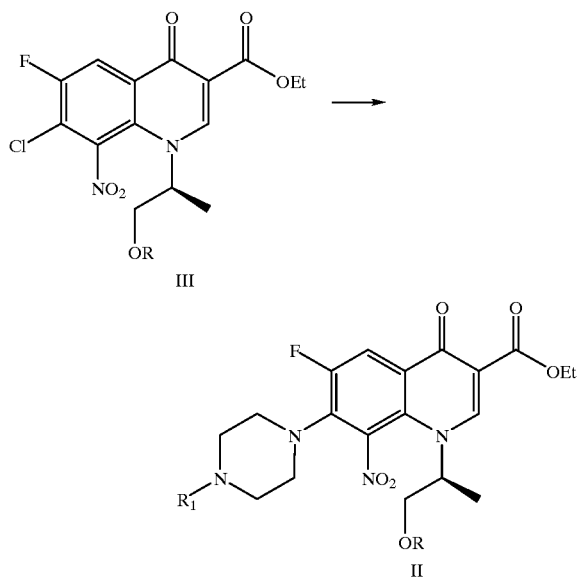

wherein,

X and R, represent the same above.

The compound(III) is reacted with 1.0~3.0 mole equivalents of piperazine or N-mono-substituted-piperazine to obtain a novel compound(II), in the presence of an organic polar solvent and 2.0~5.0 mole equivalents of a base at a temperature range of 18° C. to 120° C. In the carrying out the said reaction, the compound(III) may be employed in a purified state or non-purified state and, the organic solvent includes DMF, DMSO, dioxane, acetonitrile, tetrahydrofuran and acetone, and the base includes metal carbonate, metal bicarbonate, metal alkoxide, DBU, DABCO, DBN, pyridine, dimethylaminopyridine and trimethylamine, where the metal carbonate, the metal bicarbonate and the metal alkoxide are the same above.

The piperazine or N-mono-substituted-piperazine is represented by the following formula(VIII)

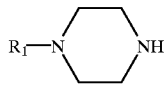

wherein, $R_1$, represents the same above.

The substituted-piperazine includes N-methypiperazine, N-ethylpiperazine, N-n-propylpiperazine, N-isopropylpiperazine, N-t-butylpiperazine, N-sec-butylpiperazine, N-n-butylpiperazine, N-isobutylpiperazine, N-t-pentylpiperazine, N-n-pentylpiperazine, N-isopentylpiperazine and N-neopentylpiperazine.

(4) Step 4: Preparation of (−)pyridobenzoxazine Carboxylic Acid Derivative(I)

The compound(II) is converted to a compound(I) by hydrolysis and cyclization of compound (II) via one or two steps.

In carrying out the said reaction via one step, the compound(I) is obtained by refluxing the compound(II) in the presence of 3.0~6.0 mole equivalents of metal hydroxide and an organic solvent with heating. The metal hydroxide includes potassium hydroxide and sodium hydroxide, and the organic solvent includes alcohol, tetrahydrofuran and a mixed solvent of one of the said solvent and water. In the case of employing the mixed solvent of alcohol and water, mixing ratio may be 100:0 to 25:75 (v/v), while in the case of the mixed solvent of tetrahydrofuran and water, mixing ratio of tetrahydrofuran and water, it may be 100:0 to 25:75 (v/v).

In the carrying out the said reaction via two steps, as shown in following reaction scheme, the compound(II) was hydrolyzed to give an intermediate compound(II-1), which is, in turn, converted to the compound(I) by hydrolysis and cyclization of compound(II-1) in a purified or non-purified state. In addition, the compound(II) was hydrolyzed to form an intermediate compound(II-2), which is, in turn, converted to the compound(I) by cyclization of compound(II-2) in a purified or non-purified state.

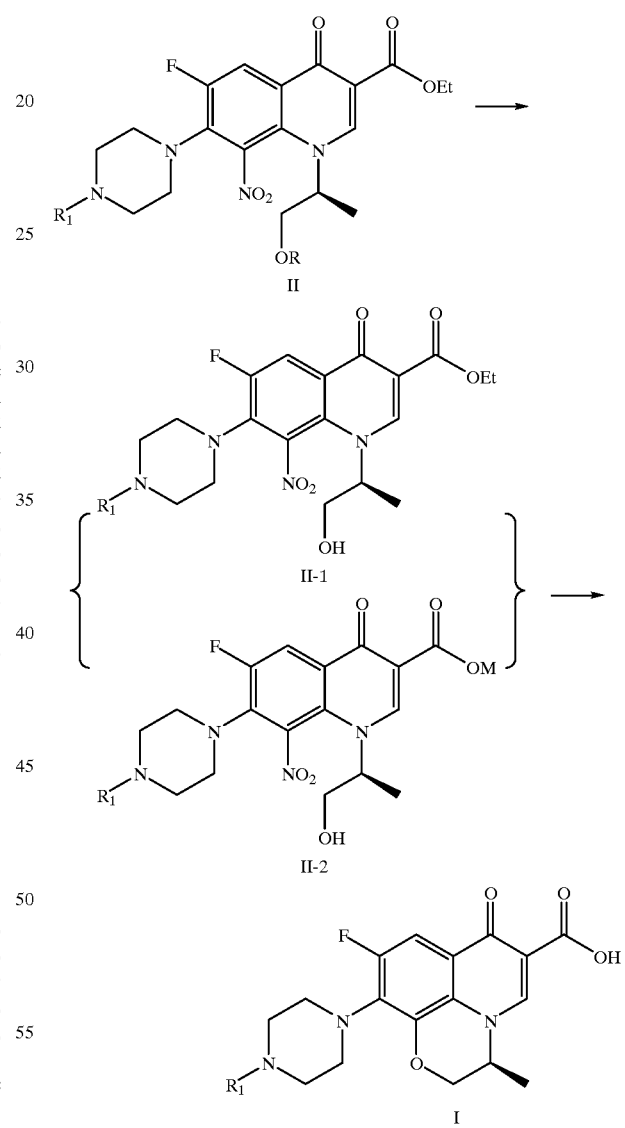

wherein,

R and $R_1$ represent the same above; and,

M represents metal atom such as potassium and sodium.

The compound(II) is reacted with 1.0~2.0 mole equivalents of metal carbonate in a mixed solvent of alcohol and water to give an intermediate compound(II-1), where the mixing ratio of alcohol and water in the mixed solvent may be 100:0 to 25:75 (v/v), and the metal carbonate includes potassium carbonate and sodium carbonate.

Further, the compound(II) is reacted with 2.0~4.0 is mole equivalents of metal hydroxide in alcohol to give an intermediate compound(II-2), where the metal hydroxide includes potassium hydroxide and sodium hydroxide.

The compound(I) is obtained by refluxing the intermediate compound(II-1) or (II-2) in the presence of 1.0~3.0 mole equivalents of metal hydroxide and an organic solvent, where the metal hydroxide includes potassium hydroxide and sodium hydroxide, and the organic solvent includes alcohol, tetrahydrofuran and a mixed solvent of one of the said solvent and water. In the case of employing the mixed solvent of alcohol and water, mixing ratio of alcohol and water may be 100:0 to 25:75(v/v), while in the case of the mixed solvent of tetrahydrofuran and water, it may be 100:0 to 25:75(v/v).

The present invention is further illustrated by the following examples, which should not be taken to limit the scope of the invention.

EXAMPLE 1

(+)Ethyl 2-(2,4-dichloro-3-nitro-5-fluorobenzoyl)-3-((1-acetoxypropy-2(S)-yl) amino]acrylate (IV, X=Cl, R=COMe)

35.0 g (85 mmol) of (+)ethyl 2-(2,4-dichloro-3-nitro-5-fluorobenzoyl)-3-[(1-hydroxypropy-2(S)-yl)amino] acrylate (V, X=Cl) prepared by the conventional process (see: U.S. Pat. No. 5,237,060) was dissolved in 150 ml of ethylenedichloride, and chilled to a temperature of −40° C. To the resultant was added 14.3 ml of triethylamine, then added 7.3 ml of acetylchlo-ide for 10 minutes at −40° C. with stirring for 1 hr. Finally, to the solution was 150 ml of water poured at room temperature to separate an organic layer, washed with 0.1N HCl solution(50 ml), 1N NaHCO$_3$ solution(50 ml, and NaCl solution (50 ml), subsequently dried over anhydrous MgSO4 then evaporated under a reduced pressure to give 38.4 g(100%, E/Z ~3/1) of the titled compound;

NMR(CDCl$_3$) δ (ppm): 10.99 (q, 1H), 8.20 (d, 1H), 7.17(d, 1H), 4.00–4.21 (m, 5H), 2.11 (s, 3H), 1.43 (d, 3H), 1.04 (t, 3H).

EXAMPLE 2

(+)Ethyl 2-(2,4-dichloro-3-nitro-5-fluorobenzoyl)-3-[(1-ethoxycarboxy-propy-2 (S)-yl)amino]acrylate (IV, X=Cl, R=CO$_2$Et)

17.8 g (43.4 mmol) of (+)ethyl 2-(2,4-dichloro-3-nitro-5-fluorobenzoyl)-3-[(1-hydroxypropy-2 (S)-yl)amino] acrylate (V, X=Cl) was dissolved in 60 ml of dichloroethane, and chilled to a temperature of 0° C. To the resultant was added 7.9 ml of triethylamine, then a solution obtained by dissolving 5.0 ml of thylchloroformate in 20.0 ml of ethylenedichloride was added for 10 minutes at 0° C. with stirring for 3hours. Finally, to the solution was 50 ml of water poured at room temperature to separate an organic layer, washed with 0.1N HCl solution(50 ml), 1N NaHCO$_3$ solution (50 ml), and NaCl solution (50 ml), subsequently dried over anhydrous MgSO$_4$, then evaporated under a reduced pressure to obtain 20.93 g (100%, E/Z ~3/1 of the titled compound.

NMR (CDCl$_3$) δ (ppm): 11.01 (d, 1H), 8.23 (d, 1H), 7.16 (d, 1H), 4.00–4.29 (m, 7H), 1.50 (d, 3H), 1.33 (t, 3H), 1.06 (t, 3H).

EXAMPLE 3

(−)Ethyl N-(1-acetoxy-propy-2 (S)-yl)-6-fluoro-7-chloro-8-nitro-4-quinolone-3-carboxylate (III, X=Cl, R=COMe)

70 mg(0.15 mmol) of (+)ethyl 2-(2,4-dichloro-3-nitro-5-fluorobenzoyl)-3-[(1-acetoxypropy-2 (S)-yl)amino] acrylate (IV, X=Cl, R=COMe) was dissolved in 2 ml of acetonitrile. To the resultant was added 80 mg of K$_2$CO$_3$, then refluxed for 4 hours with heating. After cooling to room temperature, the solvent was evaporated under a reduced pressure and treated with 5 ml of acetic acid ethylester and 5 ml of water to obtain organic layer, dried over anhydrous MgSO$_4$ and then evaporated under a reduced pressure to give 60 mg (96%) of the titled compound.

NMR (CDCl$_3$) δ (ppm): 8.61 (s, 1H), 8.46 (d, 1H), 4.45 (m, 3H), 4.31 (dd, 1H), 4.13 (dd, 1H), 1.94 (s, 3H), 1.64 (d, 3H), 1.43 (t, 3H)

EXAMPLE 4

(−)Ethyl N-(l-acetoxy-propy-2 (S)-yl)-6-fluoro-7-(N-methylpiperazinyl)-8-nitro-4-quinolone-3-carboxylate(II, R=COMe, R$_1$=Me)

60mg (0.14 mmol) of (−)ethyl N-(1-acetoxy-propy-2 (S)-yl)-6-fluoro-7-chloro-8-nitro-4-quinolone-3-carboxylate (III, X=Cl, R=COMe) and 25 mg of K$_2$CO$_3$ were dissolved in 3ml of acetonitrile. To the resultant was added 15mg of N-methylpiperazine, then refluxed for 30 minutes with heating. After cooling to room temperature, the solvent was evaporated under a reduced pressure, then dissolved in 10 ml cf acetic acid ethyl ester to separate an organic layer, washed twice with 10 ml of water, dried over anhydrous MgSO$_4$, and evaporated under a reduced pressure to give 67 mg (100%) of the titled compound.

NMR (CDCl$_3$) δ (ppm): 8.53 (s, 1H), 8.31 (d, 1H), 4.51 (m, 1H), 4.39 (q, 2H), 4.28 (dd, 1H), 4.12 (dd, 1H), 3.24 (dd, 2H), 3.13 (dd, 2H), 2.48 (ds, 4H), 2.33 (s, 3H), 1.94 (s, 3H), 1.58 (d, 3H), 1.40 (t, 3H).

EXAMPLE 5

(−)Ethyl N-(1-a-etoxy-propy-2 (S)-yl)-6-fluoro-7-(N-methylpiperazinyl)-8-nitro-4-quinolone-3-carboxylate(II, R=COMe, R$_1$=Me)

54.5 g (0.12 mol) of (+)ethyl 2-(2,4-dichloro-3-nitro-5-fluorobenzoyl)-3-[(1-acetoxypropy-2 (S)-yl)amino] acrylate (IV, X=Cl, R=COMe) was dissolved in 360 ml of acetonitrile. To the resultant was added 41.6 g of K$_2$CO$_3$, then refluxed for 8 hours with heating. After the starting material disappeared from TLC, 14.7 ml of N-methylpiperazine was added to the solution slowly for 10 minutes, further refluxed for 30 minutes with heating and cooled to room temperature. Then, inorganic salt was removed by filtration and evaporated under a reduced pressure. and treated with 250ml of acetic acid ethyl ester and 250 ml of water to fractionate an organic layer. The organic layer was dried over anhydrous MgSO$_4$, evaporated under a reduced pressure to give 52 g (90%) of the titled compound. The compound was further purified by dissolving in 150ml of ethylacetate/hexane(½, v/v) with heating and leaving to stand at room temperature, finally to give 32 g (56%) of the pure titled compound.

NMR (CDCl$_3$) δ (ppm): 8.53 (s, 1H), 8.31 (d, 1H), 4.51 (m, 1H), 4.39 (q, 2H), 4.28 (dd, 1H), 4.12 (dd, 1H), 3.24 (dd, 2H), 3.13 (dd, 2H), 2.48 (ds, 4H), 2.33 (s, 3H), 1.94 (s, 3H), 1.58 (d, 3H), 1.40 (t, 3H).

EXAMPLE 6

(−)Ethyl N-(1-ethoxycarboxy-propy-2(S)-yl)-6-fluoro-7-(N-methylpiperazinyl)-8-nitro-4-quinolone-3-carboxylate(II, R=$CO_2$Et, $R_1$=Me)

20.93 g (45.3 mmol) of (+)ethyl 2-(2,4-dichloro-3-nitro-5-fluorobenzoyl)-3-[(1-ethoxycarboxy-propy-2 (S)-yl) aminolacrylate(IV, X=Cl, R=$CO_2$Et) was dissolved in 130 ml of acetonitrile. To the resultant was added 12.0 g of $K_2CO_3$, and refluxed for 8 hours with heating. Then, 5.3 ml of N-methylpiperazine was further added, refluxed for 30 minutes with heating and cooled to room temperature. After the solvent was completely evaporated under a reduced pressure, dissolved in ethylacetate, washed with NaCl solution, dried over anhydrous $MgSO_4$, and further evaporated under a reduced pressure to give 12.7 g (57%) of the titled compound.

NMR ($CDCl_3$) δ (ppm): 8.56 (s, 1H), 8.29 (d, 1H), 4.55 (m, 1H), 4.39 (q, 2H), 4.36 (dd, 1H), 4.23 (dd, 1H), 4.11 (q, 2H), 3.24 (ds, 2H), 3.18 (ds, 2H), 2.49 (ds, 4H), 2.34 (s, 3H), 1.69 (d, 3H), 1.40 (t, 3H), 1.21 (t, 3H).

EXAMPLE 7

(−) 9-fluoro-3 (S)-methyl-10-(N-methyl-1-piperazinyl)-7-oxo-2,3-dihydro-7H-pyrido [1,2, 3-de][1,4]benzoxazine-6-carboxylic acid (I, $R_1$=Me).

3.2 g of (+)ethyl N-(l-acetoxy-propy-2 (S)-yl)-6-fluoro-7-(N-methylpiperazinyl)-8-nitro-4-quinolone-3-carboxylate (II, R=COMe, $R_1$=Me) was dissolved in 48 ml of ethanol. To the resultanl was added 2.25 g of potassium hydroxide, refluxed for 2 hours with heating. Then, the solvent was evaporated under a reduced pressure, and 6.7 ml of 3M AcOH solution was added to obtain a pale yellow precipitate, and added 10ml of THF while stirring. Then, the resultant solid was filtered, washed with water/THF (1/1, v/v) followed by drying to give 1.36 g (57%) of the titled compound.

NMR ($CDCl_3$) δ (ppm): 14.99 (s, 1H), 8.62 (s, 1H), 7.74 (d, 1H), 4.49 (dd, 2H), 4.35 (dd, 1H), 3.43 (m, 4H), 2.60 (d, 4H), 2.39 (5, 3H), 1.63 (d, 3H).

EXAMPLE 8

(−)Ethyl N-(1-hydroxy-propy-2(S)-yl)-6-fluoro-7-N-methylpiperazinyl)-8-nitro-4-quinolone-3-carboxylate(II-1, R=H)

1.38 g (10 mmnol) of $K_2CO_3$ was dissolved in 10 ml of water, and added 2.39 g (5 mmol) of (−)ethyl N-(1-acetoxy-propy-2 (s)-yl)-6-fluoro-7-N-methylpiperazinyl)-8-nitro-4-quinolone-3-carboxylate(II, R=COMe, $R_1$=Me). 7.5 ml of methanol was added and stirred for 1.5 hours at room temperature. To the precipitate thus obtained was added 10 ml of water, and subsequently filtered and washed with water. Then, the resultant solid was dried to give 2.1 g (96%) of the titled compound.

NMR ($CDCl_3$) δ (ppm): 8.72 (s, 1H), 7.74 (d, 1H), 4.46 (m, 1H), 4.37 (q, 2H), 4.19 (m, 1H), 3.92 (m, 1H), 3.75 (m, 2H), 3.25 (ds, 2H), 3.14 (ds, 2H), 2.52 (ds, 4H), 2.37 (s, 3H), 1.64 (d, 3H), 1.40 (t, 3H)

EXAMPLE 9

(−)Potassium N-(1-hydroxy-propy-2(S)-yl)-6-fluoro-7-N-methylpiperazinyl)-8-nitro-4-quinolone-3-carboxylate(II-2, R=H).

0.935 g (15 mmol) of KOH was dissolved in 18 ml of 95% ethanol, added 2.39 g (5 mmol) of (−)ethyl N-(1-acetoxy-propy-2 (S)-yl)-6-fluoro-7-N-methyl-piperazinyl)-8-nitro-4-quinolone-3-carboxylate(II, R=COMe, $R_1$, =Me), and stirred for 2 hours at room temperature. Then, the precipitate thus obtained was filtered, washed with 10 ml of 95% ethanol and the resultant solid was dried to give 2.07 g (93%) of the titled compound.

NMR ($D_2O$) δ (ppm): 8.45 (s, 1H), 8.14 (d, 1H), 4.28 (m, 1H), 3.67 (d, 2H), 3.21 (ds, 2H), 3.07 (ds, 2H), 3.14 (ds, 2H), 2.46 (ds, 4H), 2.18 (s, 3H), 1.42 (t, 3H)

EXAMPLE 10

(−)9-fluoro-3(S)-methyl-10-(N-methyl-piperazinyl)-7-oxo-2,3-dihydro-7H-pyrido[2,3-de][1,4]benzoxazine-6-carboxylic acid(I, $R_1$=Me).

5.1 g (11.42 mmol) of (−)potassium N-(1-hydroxy-propy-2(S)-yl)-6-fluoro-7-N-methylpiperazinyl)-8-nitro-4-quinolone-3-carboxylate(II-1, R=H) was dissolved in 34 ml of methanol. To the solution was added 1.07 g of potassium hydroxide, then refluxed for 2.5 hours with heating. The solvent was evaporated under a reduced pressure, then 5.7 ml of 3M AcOH solution was subsequently added to give a pale yellow precipitate, and added 10 ml of THF while stirring. Then, the resultant solid was filtered, washed with water/THF(1/1, v/v) and followed by drying to give 3.0 g (73%) of the titled compound.

NMR ($CDCl_3$) δ (ppm): 14.99 (s, 1H), 8.62 (s, 1H), 7.74 (d, 1H), 4.49 (dd, 2H), 4.35 (dd, 1H), 3.43 (m, 4H), 2.60 (d, 4H), 2.39 (s, 3H), 1.63 (d, 3H).

EXAMPLE 11

(−)9-fluoro-3(S)-methyl-10-(N-methyl-1-piperazinyl)-7-oxo-2,3-dihydro-7H-pyrido[1,2,3-de](1,4]benzoxazine-6-carboxylic acid(I, $R_1$=Me).

5.0 g of (−)ethyl N-(1-hydroxy-propy-2(S)-yl)-6-fluoro-7-N-methylpiperazinyl)-8-nitro-4-quinolone-3-carboxylate (II-1, R=H) was reacted in the same manner as in Example 10 to give about 3.0 g (73%) of the titled compound.

NMR ($CDCl_3$) δ (ppm): 14.99 (s, 1H), 8.62 (s, 1H), 7.74 (d, 1H), 4.49 (dd, 2H), 4.35 (dd, 1H), 3.43 (m, 4H), 2.60 (d, 4H), 2.39 (s, 3H), 1.63 (d, 3H).

As clearly illustrated and demonstrated above, the present invention provides a novel process for preparing optically active (−)pyridobenzoxazine carboxylic acid derivatives or pharmaceutically acceptable salt thereofs. According to the present invention, optically active (−)pyridobenzoxazine carboxylic acid derivatives can be manufactured from the low-priced 4-chloro-5-fluoro-2-halo-3-nitrobenzoic acid in a simple and economical manner.

What is claimed is:

1. A process for preparing optically active (−)pyridobenzoxazine carboxylic acid derivative (I) or pharmaceutically acceptable salt thereof, the process comprising:

i) reacting a compound of formula (V) with a reactive material of formula (VI) or (VII) in the presence of a base to obtain a compound of formula (IV);

ii) converting the compound (IV) obtained in step i) in an organic polar solvent in the presence of a base to obtain a compound of formula (III);

iii) reacting the compound (III) obtained in step ii) with piperazine or N-mono-substituted-piperazine in an organic polar solvent in the presence of a base to obtain a compound of formula (II); and iv) hydrolyzing and cyclizing the compound (II) obtained in said step iii) in an organic solvent in the presence of metal hydroxide to give a compound of formula (I)

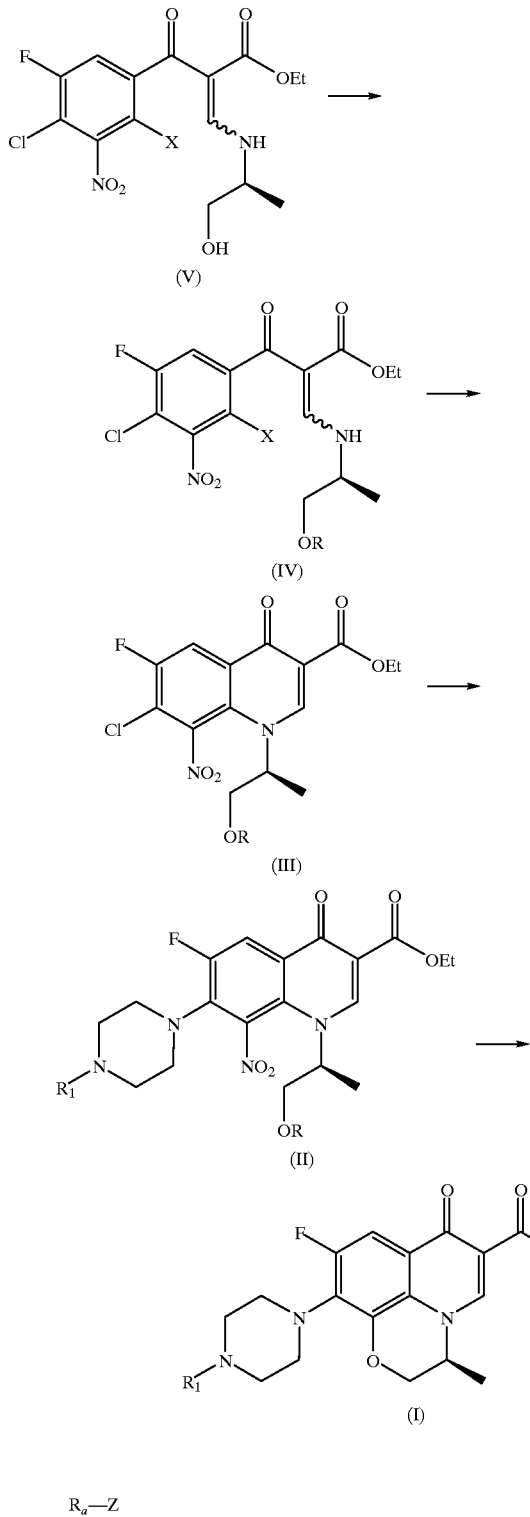

wherein,

X represents a halogen atom;

Z represents a leaving group;

Y represents an oxygen or a sulfur atom;

$R_a$ represents —C (=O) —$R_2$, wherein $R_2$ represents an alkyl group having 1 to 5 carbon atoms, phenyl group, substituted phenyl group, alkoxy group having 1 to 5 carbon atoms, cycloalkoxy group having 3 to 5 carbon atoms, phenoxy group, substituted phenoxy group, primary or secondary amine group or alkylthio group having 1 to 5 carbon atoms;

$R_b$ represents alkyl group having 1 to 5 carbon atoms, phenyl group or substituted phenyl group;

R represents the same as $R_a$ above or $R_b$—NH—C (=Y), wherein $R_b$ and Y represent the same as above; and, $R_1$ represents hydrogen atom or alkyl group having 1 to 5 carbon atoms.

2. The process of claim 1, wherein the base is selected from the group consisting of metal carbonates, metal bicarbonates, metal alkoxides DBU (1,8-diazabicyclo undec-7-ene), DABCO (1,4-diazabicyclo octane, DBN (1,5-diazabicyclo non-5-ene), pyridine, dimethylaminopyridine, and trimethylamine.

3. The process of claim 1, wherein the reactive material of formula (VI) is selected from the group consisting of acylhalides, carboxylic anhydrides, alkylchloroformates, cycloalkylchloroformates, alkylcarbonates, cycloalkylcarbonates, phenylchloroformates, and substituted phenylchloroformates.

4. The process of claim 1, wherein the reactive material; of formula (VII) is isocyanate.

5. The process of claim 1, wherein the organic polar solvent in said steps ii) and iii) is selected from the group consisting of DMF(N,N'-dimethylformamide), DMSO (dimethylsulfoxide), dioxane, acetonitrile, tetrahydrofuran, and acetone.

6. The process of claim 1, wherein the organic solvent in the step iv) is selected from the group consisting of alcohol, tetrahydrofuran, and a mixed solvent of one of the said solvents and water.

7. The process of claim 1, wherein the compound (III) is employed in the step iii) in a purified state.

8. The process of claim 1, wherein the compound (III) is hydrolyzed to an intermediate compound of formula (II1), which is subsequently hydrolyzed and cyclized to give the compound (I):

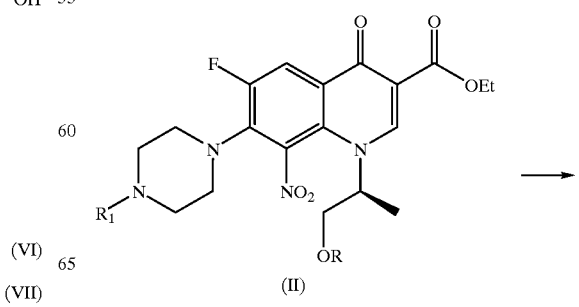

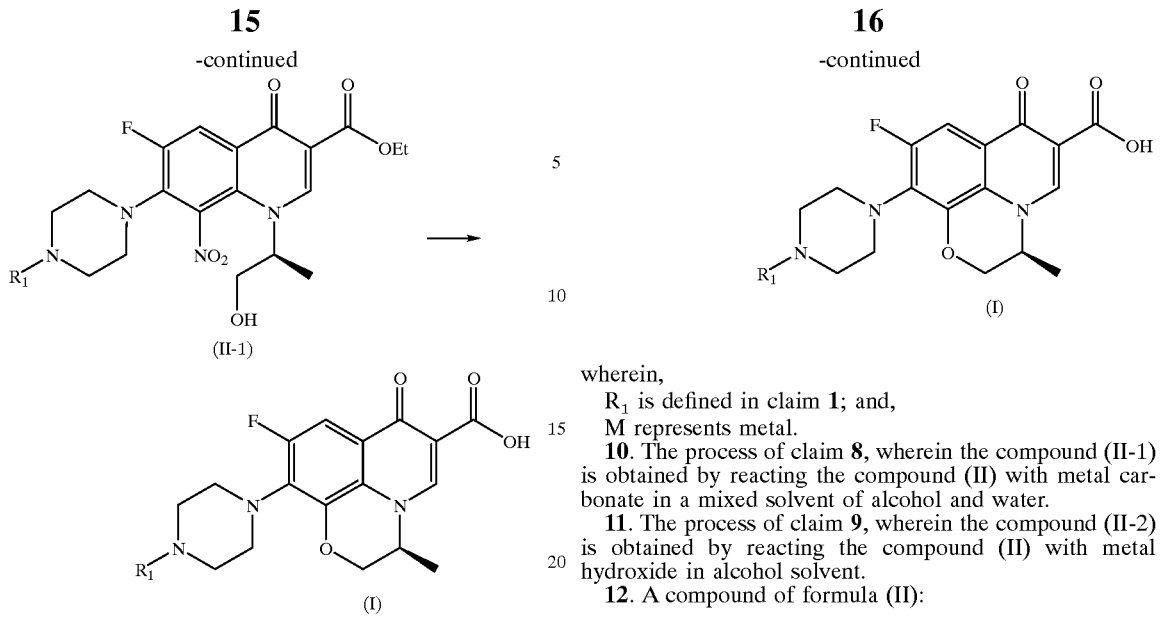

(II-1)

wherein,

R₁, is defined in claim 1.

9. The process of claim 1, wherein the compound (II) is hydrolyzed to an intermediate compound of formula (II-2), which is subsequently cyclized to give the compound (I):

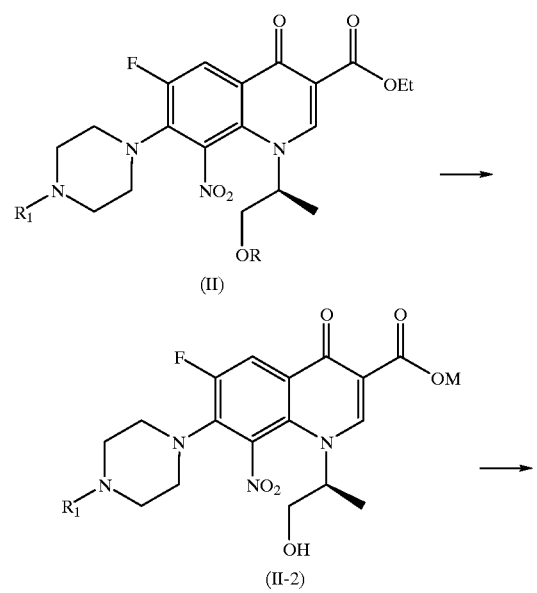

(II)

(II-2)

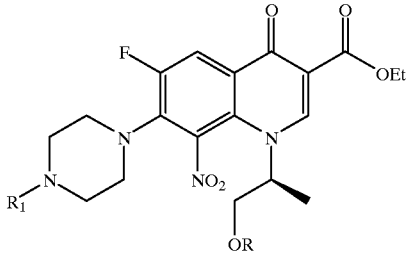

(I)

wherein,

R₁ is defined in claim 1; and,

M represents metal.

10. The process of claim 8, wherein the compound (II-1) is obtained by reacting the compound (II) with metal carbonate in a mixed solvent of alcohol and water.

11. The process of claim 9, wherein the compound (II-2) is obtained by reacting the compound (II) with metal hydroxide in alcohol solvent.

12. A compound of formula (II):

(II)

wherein R represents —C(=O)—R₂, wherein R₂ represents an alkyl group having 1 to 5 carbon atoms, phenyl group, substituted phenyl group, alkoxy group having 1 to 5 carbon atoms, cycloalkoxy group having 3 to 5 carbon atoms, phenoxy group, substituted phenoxy group, primary or secondary amine group or alkylthio group having 1 to 5 carbon atoms or R represents R$_b$—NH—C(=Y) wherein R$_b$ represents an alkyl group having 1 to 5 carbon atoms, phenyl group or substituted phenyl group and Y represents an oxygen or a sulfur atom: and R₁ represents a hydrogen atom or an alkyl group having 1 to 5 carbon atoms.

13. (−)(Ethyl N-(1-acetoxy-propy-2 (S)-yl)-6-fluoro-7-(N-methylpiperazinyl)-8-nitro-4-quinolone-3-carboxylate.

14. The process of claim 1, wherein the reactive material of formula (VII) is isothiocyanate.

15. The process of claim 1, wherein the compound (III) is employed in the step iii) in a non-purified state.

* * * * *

UNITED STATES PATENT AND TRADEMARK OFFICE
CERTIFICATE OF CORRECTION

PATENT NO.    : 6,316,618 B1                                                          Page 1 of 1
DATED         : November 13, 2001
INVENTOR(S)   : Young-Jun Park et al.

It is certified that error appears in the above-identified patent and that said Letters Patent is hereby corrected as shown below:

<u>Column 14,</u>
Line 51, please replace "(III)" with -- (II) --.
Line 52, replace "(II 1)" with -- (II-1) --.

Signed and Sealed this

Tenth Day of June, 2003

JAMES E. ROGAN
*Director of the United States Patent and Trademark Office*